(12) United States Patent
Wang

(10) Patent No.: US 6,991,638 B2
(45) Date of Patent: Jan. 31, 2006

(54) EAR VACUUM

(75) Inventor: Haier Wang, Cixi (CN)

(73) Assignee: Leivaire Inc., Ontario (CA)

( * ) Notice: Subject to any disclaimer, the term of this patent is extended or adjusted under 35 U.S.C. 154(b) by 411 days.

(21) Appl. No.: 10/300,896

(22) Filed: Nov. 21, 2002

(65) Prior Publication Data

US 2003/0097142 A1    May 22, 2003

(51) Int. Cl.
*A61F 11/00* (2006.01)
(52) U.S. Cl. ........................................... 606/162
(58) Field of Classification Search .............. 606/162, 606/161, 160; 604/35, 73, 315, 319
See application file for complete search history.

(56) References Cited

U.S. PATENT DOCUMENTS 6,059,803 A * 5/2000 Spilman ................ 606/162
6,406,484 B1 * 6/2002 Lang ..................... 606/162
6,517,511 B2 * 2/2003 Yao ....................... 606/162

* cited by examiner

Primary Examiner—Kevin T. Truong
(74) Attorney, Agent, or Firm—Birch, Stewart, Kolasch & Birch, LLP

(57) ABSTRACT

An ear cleaner is provided to clean ears more safely. It comprises first and second body members, the first body member comprising two sections, a screen separating the two sections, one of such sections having a tube communicating with its interior and being adapted for insertion in an ear, said one section enclosing a space for receiving debris extracted from the ear and being separably connected to the other section to permit removal of such debris, the other section comprising a fan to provide a vacuum for removing debris from the ear, the second body member acting as a handle for the first body member and providing a receptacle for batteries to energize the fan. Preferably contamination is avoided by mounting the cleaner on a pedestal.

20 Claims, 2 Drawing Sheets

_US 6,991,638 B2_

EAR VACUUM

FIELD OF THE INVENTION

This invention relates to an ear cleaner.

BACKGROUND OF THE INVENTION

In everyday life we clean the cerumen with an instrument or cotton swab. Probing a rigid object into the ear hole is apt to injure the ear hole and the cleaning is never thorough. The reason is that neither the tool nor the way it is used is scientific. Very often it causes ear diseases. An extreme situation would be causing deafness by damaging the eardrum. Another unsafe situation is when, after a shower, we use a cotton swab to absorb water left in the ear hole.

Both when an instrument is used or a cotton swab, there is a danger of contamination resulting in infection.

BRIEF SUMMARY OF THE INVENTION

An object of the invention is to provide an ear cleaner which will use a vacuum to clean the cerumen and water in the ear hole. This can avoid injury as compared with mechanical devices that scrape the ear. It is safe and has good cleaning effect.

A further object is to provide a rational design, mini-size, and provide portability so as to be suitable for home use, travel and beauty store applications.

In the preferred embodiment of the invention, the ear cleaner is removably mounted on a pedestal, so that the part that penetrates the ear will be free from contamination from contact with other objects.

In accordance with this invention, there is provided an ear cleaner comprising first and second body members, the first body member comprising two sections, a screen separating the two sections, one of such sections having a tube communicating with its interior and being adapted for insertion in an ear, said one section enclosing a space for receiving debris extracted from the ear and being separably connected to the other section to permit removal of such debris, the other section comprising a fan to provide a vacuum for removing debris from the ear, the second body member acting as a handle for the first body member and providing a receptacle for batteries to energize the fan.

In accordance with a preferred aspect of the invention, the ear cleaner is removably mounted on a pedestal so that the part that contacts the ear will be maintained free from contamination.

BRIEF DESCRIPTION OF THE DRAWINGS

The accompanying drawings, which are incorporated in and constitute a part of the specification, illustrate a preferred embodiment of the invention and, together with a general description given above and the detailed description of the preferred embodiment given below, serve to explain the principles of the invention.

In the drawings which illustrate the preferred embodiment of the invention.

DETAILED DESCRIPTION OF THE INVENTION

Figure 1:
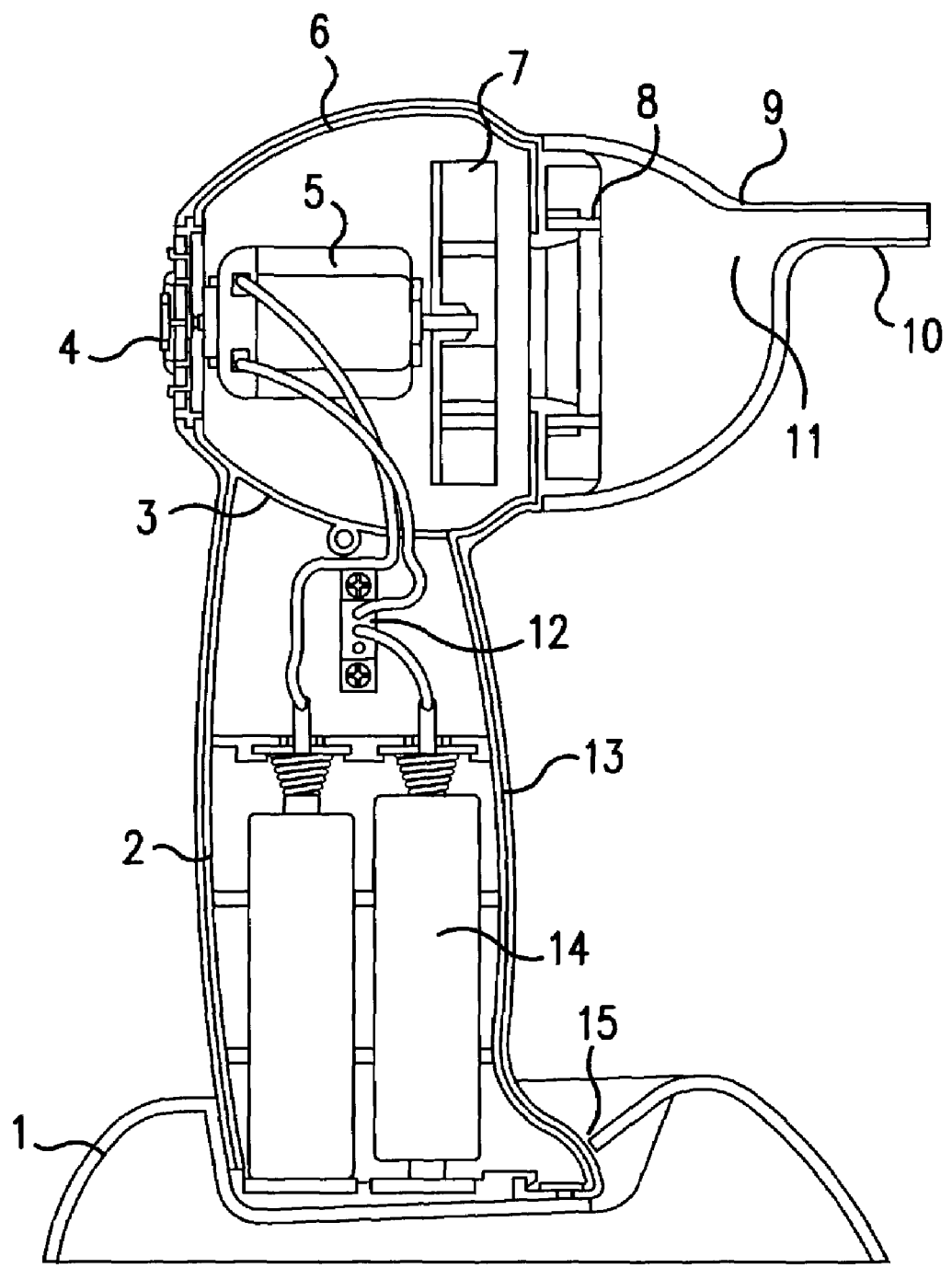
FIG. 1 is a sectional elevation view of an ear cleaner in accordance with this invention.
Figure 2:
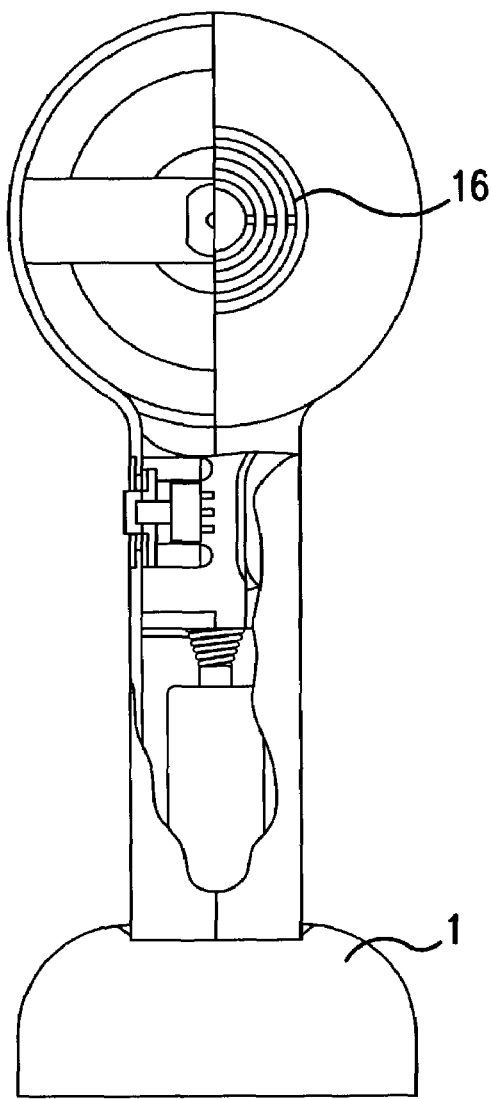
FIG. 2 is a left sectional elevation view of an ear cleaner in accordance with this invention.
Figure 3:
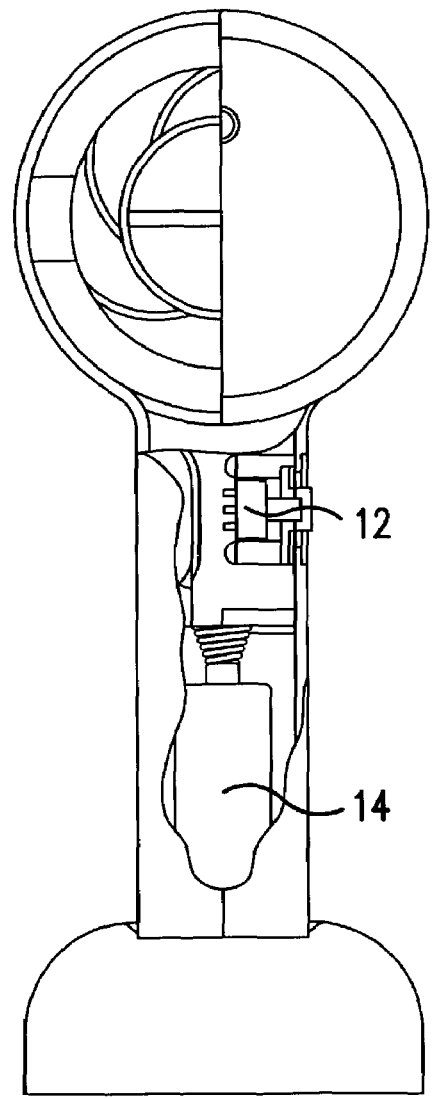
FIG. 3 is a right sectional elevation view of an ear cleaner in accordance with this invention.

In the drawings, the ear cleaner comprises a first body member 3 and a second body member 2. The first body member comprises two sections; one of such sections 9 has a bugle shaped tube 10 communicating with its interior and being adapted for insertion into the ear. If desired, tube 10 can be fitted with a removable silicon nozzle (not shown).

Tube 10 communicates with a space 11 for receiving debris extracted from the ear. Section 9 is removably attached to the second section 6 so that debris can easily be emptied from space 11.

A mesh screen 8 separates sections 6 and 9 and results in debris being deposited in space 11.

Section 6 encloses motor 5 which drives impeller 7 to create a vacuum in space 11, consequently extracting matter from the ear. There is an outlet 4.

Body 2 is joined to body 3 to provide a handle. It contains batteries 14 which energize motor 5. A switch 12 is mounted on body 13.

At the base of handle 2 there is a pedestal 1 having a recess to receive the handle. As shown at 15, handle 2 has a projection engaged by a spring clip removably to hold the ear cleaner in an upright position, as shown, until it is to be used, thereby avoiding contamination.

To operate this cleaner, turn on the power switch, check the slight turning sound of the motor. Put the nozzle close to your ear, slightly turn it and then probe into ear hole little by little.

When power is on, the motor starts and turns the centrifugal impeller which runs at high speed. Air in the shell is ventilated out through the rear cover, forming a vacuum in the chamber. Negative pressure and air pressure create a pressure difference. Because the shell is connected to the nozzle, water or cerumen in the ear hole is sucked into the nozzle, falling to the bottom of the cover due to the mesh blocking. Thus, the goal of ear cleaning is accomplished.

As is evident from the above description, a wide variety of ear vacuum devices may have been envisioned from the device described herein and additional advantages and modifications will readily occur to those skilled in the art. The invention in its broader aspects is, therefore, not limited to the specific details, representative apparatus and illustrative examples shown and described. Accordingly, departures from such details may be made without departing from the spirit or scope of the applicant's general inventive concept.

What is claimed is:

1. An ear cleaner comprising:
   first and second body members, the first body member comprising two sections with a first section forming an enlarged interior area at a central portion thereof and an outwardly projecting portion that is tapered outwardly towards a front portion of the ear cleaner;
   a screen separating the two sections, said screen being disposed in substantially the central portion of said first body member;
   said first section having a tube extending from the tapered outwardly projecting portion for communicating with the enlarged interior area and being adapted for insertion in an ear, said first section enclosing a space for receiving debris extracted from the ear and being separably connected to the second section to permit removal of such debris:
   the second section including a fan to provide a vacuum for removing debris from the ear, the second body member acting as a handle for the first body member and providing a receptacle for batteries to energize the fan.

2. The ear cleaner as in claim 1, wherein said ear cleaner is removably mounted on a pedestal.

3. The ear cleaner as in claim 2, wherein the base of the second body member has a laterally extending wedge shaped projection, the pedestal has a recess to receive the bottom end of the handle including such projection and means are provided separately to engage such wedge shaped projection.

4. The ear cleaner according to claim 1, wherein said first body member is substantially circular in cross-section and a mating portion of said first section being substantially equal in cross-section to a mating portion of said second section for forming said space for receiving debris.

5. The ear cleaner according to claim 1, wherein said screen extends between the first section and the second section for defining one side of said space for receiving debris.

6. The ear cleaner according to claim 1, wherein said fan is mounted adjacent to said screen and includes at least one fan blade extending in an enlarged interior area of said second section and being arranged to be substantially in a central portion thereof.

7. The ear cleaner according to claim 1, and further including an outlet being formed in a rear portion of said second section for discharging air flow from the fan.

8. The ear cleaner according to claim 1, wherein said tube extending from said first section is disposed substantially adjacent to an upper surface of said first section for forming a lower portion of said first section for receiving debris.

9. The ear cleaner according to claim 1, wherein said screen is secured to said second section of said first body member and wherein said first section is mounted to be secured to said second section directly in the area of said screen.

10. The ear cleaner according to claim 1, wherein said first and second sections are substantially circular in cross-section in an area where the first and second sections are secured relative to each other and said second section tapers downwardly to a rear portion of said first body member.

11. An ear cleaner comprising:
a first body member and second body member;
said first body member including a first section and a second section;
said first section forming an enlarged interior area at a central portion thereof and an outwardly projecting portion that is tapered outwardly towards a front portion of the ear cleaner;
said second section forming an enlarged interior area at a central portion thereof and an outwardly projecting portion that is tapered outwardly towards a rear portion of the ear cleaner;
a screen separating the first section and the second section, said screen being disposed in substantially the central portion of said first body and extending to form a screen closure between the first section and the second section;
said first section having a projecting member extending from the tapered outwardly projecting portion for providing communication with the enlarged interior area and being adapted for insertion in an ear, said first section enclosing a space for receiving debris extracted from the ear and said first section being removably mounted relative to the second section to permit the first section to be disconnected from the second section for removal of debris; and
a fan operatively mounted within the second section for providing a vacuum for removing debris from the ear;
said second body member acting as a handle for the first body member and being adapted to receive batteries to energize the fan.

12. The ear cleaner as in claim 11, wherein said ear cleaner is removably mounted on a pedestal.

13. The ear cleaner as in claim 12, wherein the base of the second body member has a laterally extending wedge shaped projection, the pedestal has a recess to receive the bottom end of the handle including such projection and means are provided separately to engage such wedge shaped projection.

14. The ear cleaner according to claim 11, wherein said first body member is substantially circular in cross-section and a mating portion of said first section being substantially equal in cross-section to a mating portion of said second section for forming said space for receiving debris.

15. The ear cleaner according to claim 11, wherein said screen extends between the first section and the second section for defining one side of said space for receiving debris.

16. The ear cleaner according to claim 11, wherein said fan is mounted adjacent to said screen and includes at least one fan blade extending in an enlarged interior area of said second section and being arranged to be substantially in a central portion thereof.

17. The ear cleaner according to claim 11, and further including an outlet being formed in a rear portion of said second section for discharging air flow from the fan.

18. The ear cleaner according to claim 11, wherein said tube extending from said first section is disposed substantially adjacent to an upper surface of said first section for forming a lower portion of said first section for receiving debris.

19. The ear cleaner according to claim 11, wherein said screen is secured to said second section of said first body member and wherein said first section is mounted to be secured to said second section directly in the area of said screen.

20. The ear cleaner according to claim 11, wherein said first and second sections are substantially circular in cross-section in an area where the first and second sections are secured relative to each other and said second section tapers downwardly to a rear portion of said first body member.

* * * * *